United States Patent [19]

Debono

[11] 4,293,483

[45] Oct. 6, 1981

[54] DERIVATIVES OF A-30912A NUCLEUS

[75] Inventor: Manuel Debono, Indianapolis, Ind.

[73] Assignee: Eli Lilly and Company, Indianapolis, Ind.

[21] Appl. No.: 181,030

[22] Filed: Aug. 25, 1980

Related U.S. Application Data

[63] Continuation-in-part of Ser. No. 103,149, Dec. 13, 1979, abandoned.

[51] Int. Cl.³ .......................................... C07C 103/52
[52] U.S. Cl. ........................................... 260/112.5 R
[58] Field of Search ................................ 260/112.5 R

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgins et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 568386 | 4/1972 | Belgium | 260/112.5 R |
| 834289 | 10/1974 | Belgium | 260/112.5 R |
| 859067 | 2/1977 | Belgium | 260/112.5 R |
| 866095 | 4/1977 | Belgium | 260/112.5 R |
| 851310 | 8/1977 | Belgium | 260/112.5 R |

OTHER PUBLICATIONS

The Journal of Antibiotics, vol 29, No. 12, 1339–1340, 1976.
Agr. Biol. Chem. 37 (11), 2455–2463, 1973.
Agr. Biol. Chem. 37 (12), 2709–2717, 1973.
Agr. Biol. Chem. 38 (3), 521–529, 1974.
Agr. Biol. Chem. 38 (10), 1767–1777, (1974).
The Journal of Biochemistry, vol. 56, No. 4, 1964, 335–343.
The Journal of Antibiotics, vol. 31, No. 4, 373–374, (1978).
The Journal of Antibiotics (1975), 764–769, vol. 28, No. 10.
The Journal of Antibiotics 1976, 380–389, vol. 29, No. 4.
The Journal of Antibiotics 1976, 1268–1274, vol. 29, No. 12.
The Journal of Antibiotics, vol. 29, No. 12, 1275–1280, 1976.
Helvetica Chimica Acta, vol. 57, fasc. 8 (1974), 2459–2477.
Tetrahedran Letters, No. 46, pp. 4147–4150, 1976.
Helvetica Chimica Acta, vol. 62, fasc. 4 (1979), 1252–1266.

*Primary Examiner*—Delbert R. Phillips
*Attorney, Agent, or Firm*—Nancy J. Harrison; Arthur R. Whale

[57] ABSTRACT

Compounds of the formula

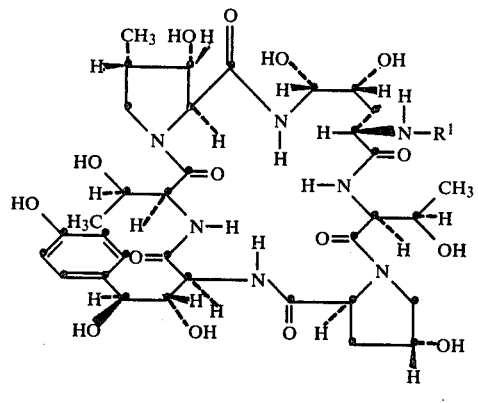

wherein
$R^1$ is an N-alkanoyl amino acyl group of the formula

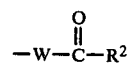

wherein:
W is a divalent aminoacyl radical of the formula:

(a)

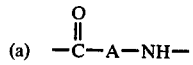

wherein A is $C_1$–$C_{10}$ alkylene or $C_5$–$C_6$ cycloalkylene;

(b)

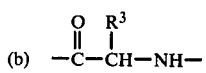

wherein $R^3$ is hydroxymethyl, hydroxyethyl, mercaptomethyl, mercaptoethyl, methylthioethyl, 2-thienyl, 3-indole-methyl, phenyl, benzyl, or substituted phenyl or substituted benzyl in which the benzene ring thereof is substituted with chloro, bromo, iodo, nitro, $C_1$–$C_3$ alkyl, hydroxy, $C_1$–$C_3$ alkylthio, carbamyl, or $C_1$–$C_3$ alkylcarbamyl;

(c)

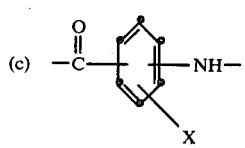

wherein X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl;

(d) 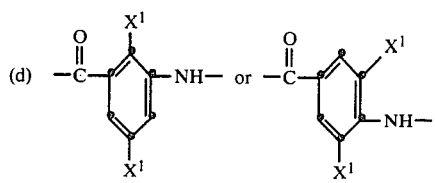
wherein $X^1$ is chloro, bromo, or iodo;
(e) 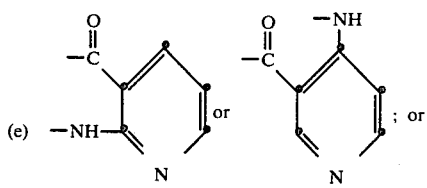 ; or
(f) 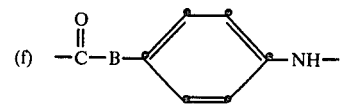
wherein B is a divalent radical of the formula: $-(CH_2)_n-$, wherein n is an integer from 1 to 3; $-CH=CH-$; $-CH=CH-CH_2-$;
or 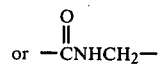
and $R^2$ is $C_1$–$C_{17}$ alkyl or $C_2$–$C_{17}$ alkenyl; have antifungal activity.
25 Claims, No Drawings

DERIVATIVES OF A-30912A NUCLEUS

CROSS-REFERENCE TO RELATED APPLICATION

This application is a continuation-in-part of application Ser. No. 103,149, filed Dec. 13, 1979, now abandoned.

BACKGROUND OF THE INVENTION

This invention relates to novel semisynthetic antifungal compounds which are prepared by the acylation of the cyclic peptide nucleus produced by the enzymatic deacylation of antibiotic A30912 factor A.

Antibiotic A-30912 factor A is an antifungal cyclic peptide having the formula:

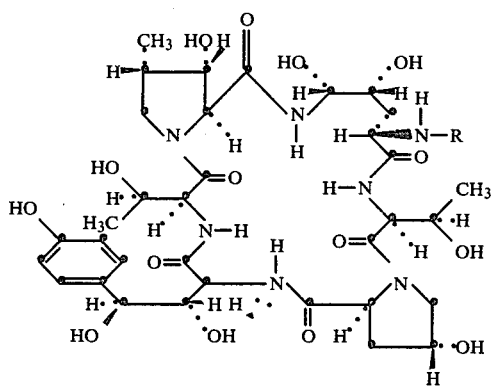

wherein R is the linoleoyl group

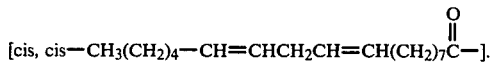

[cis, cis—CH$_3$(CH$_2$)$_4$—CH=CHCH$_2$CH=CH(CH$_2$)$_7$C—].

Throughout this application, the cyclic peptide formulas, such as formula I, assume that the amino acids represented are in the L-configuration. The factor is isolated from the A30912 complex which contains other factors arbitrarily designated factors B, C, D, E, and G. The A-30912 complex and the individual factors A through G are described by M. Hoehn and K. Michel in U.S. Pat. No. 4,024,245. Factor A is identical to antibiotic A-22802 which is described by C. Higgins and K. Michel in U.S. Pat. No. 4,024,246. Factor A has also been found to be identical to antibiotic echinocandin B [see F. Benz et al., *Helv. Chim. Acta*, 57, 2459 (1974) and Swiss Pat. No. 568,386] and to antibiotic SL 7810/F [see C. Keller-Juslen et al. *Tetrahedron Letters*, 4147 (1976) and Belgium Pat. No. 834,289].

Antibiotic A-30912 factor A is prepared by fermentation using one of several different organisms, namely: (a) *Aspergillus rugulosus* NRRL 8113 (see U.S. Pat. No. 4,024,245); (b) *Aspergillus nidulans* NRRL 8112 (see U.S. Pat. No. 4,024,246); (c) *Aspergillus nidulans* var. echinulatus A-32204 as described in Swiss Pat. No. 568,386; (d) *Aspergillus rugulosus* NRRL 8039 (see Belgian Pat. No. 834,289); or (e) *Aspergillus nidulans* var. roseus NRRL 11440 (see co-pending application of L. Boeck and R. Kastner, METHOD OF PRODUCING THE A-30912 ANTIBIOTICS, Ser. No. 126,078, filed Mar. 3, 1980, which is a continuation-in-part of application Ser. No. 46,744, filed June 8, 1979, (now abandoned), the entire disclosure of which is incorporated herein by reference.)

A subculture of *A. nidulans* var. roseus has been deposited and made a part of the permanent culture collection of the Northern Regional Research Laboratory, U.S. Department of Agriculture, Agricultural Research Service, Peoria, Ill. 61604, from which it is available to the public under the number NRRL 11440.

When a strain of *A. nidulans* var. roseus NRRL 11440 is used to produce A-30912 factor A, a complex of factors is obtained which for convenience is called the A-42355 antibiotic complex. A-30912 factor A is the major factor of the A-42355 antibiotic complex, while factors B, D and H are minor factors. Examples 96, 97, and 98, herein, illustrate the preparation of the A-42355 complex and the isolation and purification of A-30912 factor A therefrom. A-30912 factor H is further described in a co-pending application of Karl. H. Michel entitled ANTIBIOTIC A-30912 FACTOR H, Ser. No. 117,739, filed Feb. 1, 1980, which is a continuation-in-part of application Ser. No. 46,875, filed June 8, 1979 (now abandoned).

In the A-30912 factor A molecule (Formula I), the linoleoyl side chain (R) is attached at the cyclic peptide nucleus at the α-amino group of the dihydroxyornithine residue. Surprisingly, it has been found that the linoleoyl side chain can be cleaved from the nucleus by an enzyme without affecting the chemical intregity of the nucleus. The enzyme employed to effect the deacylation reaction is produced by a microorganism of the family Actinoplanaceae, preferably the microorganism *Actinoplanes utahensis* NRRL 12052, or a variant thereof. To accomplish deacylation, antibiotic A30912 factor A is added to a culture of the microorganism and the culture is allowed to incubate with the substrate until the deacylation is substantially complete. The cyclic nucleus thereby obtained is separated from the fermentation broth by methods known in the art. Unlike antibiotic A-30912 factor A, the cyclic nucleus (lacking the linoleoyl side chain) is substantially devoid of antifungal activity.

The cyclic nucleus afforded by the aforedescribed enzymatic deacylation of antibiotic A-30912 factor A, is depicted in Formula II.

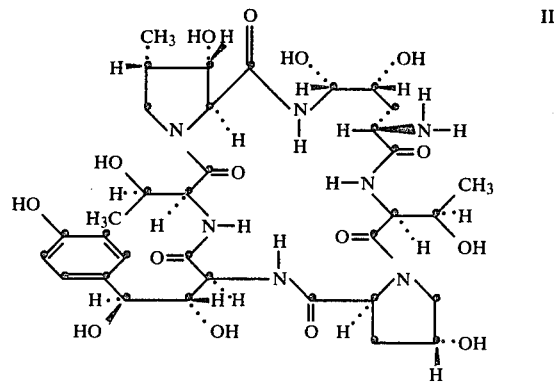

Removal of the side chain group affords a free primary α-amino group in the dihydroxyornithine residue of the cyclic peptide. For convenience, the compound having the structure given in Formula II will be referred to herein as "A-30912A nucleus." As will be apparent to those skilled in the art, A-30912A nucleus can be obtained either in the form of the free amine or of the acid addition salt. Although any suitable acid addition salt may be employed, those which are non-toxic and pharmaceutically acceptable are preferred.

The method of preparing A-30912A nucleus from antibiotic A-30912 factor A by means of fermentation using *Actinoplanes utahensis* NRRL 12052 is described in the co-pending application of Bernard J. Abbott and David S. Fukuda, entitled "A-30912A NUCLEUS", Ser. No. 103,017, which was filed Dec. 13, 1979. A continuation-in-part application of this application, with the corresponding Ser. No. 103,149, is being filed herewith this even date, the full disclosure of which is incorporated herein by reference. Example 93, herein, illustrates the preparation of A-30912A nucleus by fermentation using antibiotic A-30912 factor A as the substrate and *Actinoplanes utahensis* NRRL 12052 as the microorganism.

The enzyme produced by *Actinoplanes utahensis* NRRL 12052 may be the same enzyme which has been used to deacylate penicillins (see Walter J. Kleinschmidt, Walter E. Wright, Frederick W. Kavanagh, and William M. Stark, U.S. Pat. No. 3,150,059, issued Sept. 22, 1964).

Cultures of representative species of Actinoplanaceae are available to the public from the Northern Regional Research Laboratory under the following accession numbers:

Actinoplanes utahensis: NRRL 12052
Actinoplanes missouriensis: NRRL 12053
Actinoplanes sp.: NRRL 8122
Actinoplanes sp.: NRRL 12065
Streptosporangium roseum var. hollandensis: NRRL 12064

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. Loss of antibiotic activity is an indication that the microorganism produces the requisite enzyme for deacylation. This must be verified, however, using one of the following methods: (1) analysis by HPLC for presence of the intact nucleus; or (2) reacylation with an appropriate side chain (e.g. linoleoyl, stearoyl, or palmitoyl) to restore activity.

It is known that other antibiotic substances possess the same nucleus as that of antibiotic A-30912 factor A. These antibiotics differ from antibiotic A-30912 factor A in that different acyl groups are present in place of the linoleoyl group (R) in Formula I. Such antibiotics are: (a) tetrahydro-A-30912 factor A (tetrahydro-SL 7810/F; tetrahydro echinocandin B) described in Belgium Pat. No. 834,289 and by F. Benz et al., *Helv. Chim. Acta*, 57 2459 (1974), which compound is depicted in Formula I when R is stearoyl; and (b) aculaecin A, which is a component of the aculaecin complex (prepared by fermentation using *Aspergillus aculeatus* NRRL 8075) and is described by K. Mizuno et al., in U.S. Pat. No. 3,978,210. As is discussed in Belgium Pat. No. 859,067, in aculaecin A the palmitoyl side chain is present in place of linoleoyl. Tetrahydro-A-30912 factor A can be prepared from antibiotic A-30912 factor A by catalytic hydrogenation using $PtO_2$ in ethanol under positive pressure. Both tetrahydro-A-30912 factor A and aculaecin A can be employed as substrates for the enzymatic deacylation using the procedures herein described.

SUMMARY OF THE INVENTION

The invention sought to be patented comprehends novel compounds derived by acylating the A-30912A nucleus (Formula II). The compounds of the present invention have the chemical structure depicted in Formula III:

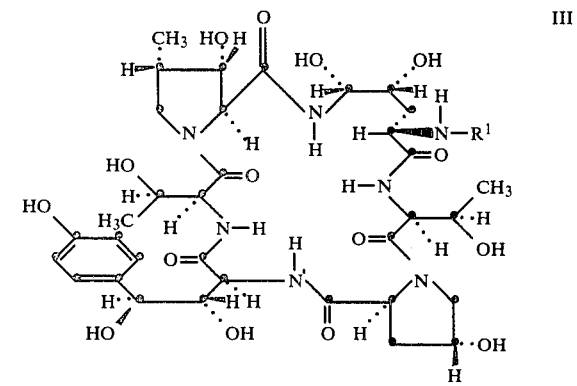

wherein $R^1$ is an N-alkanoyl amino acyl group of the formula

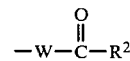

wherein:

W is a divalent aminoacyl radical of the formula:

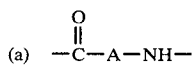

wherein A is $C_1$-$C_{10}$ alkylene or $C_5$-$C_6$ cycloalkylene;

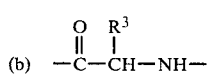

wherein $R^3$ is hydroxymethyl, hydroxyethyl, mercaptomethyl, mercaptoethyl, methylthioethyl, 2-thienyl, 3-indole-methyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamyl, or $C_1$-$C_3$ alkylcarbamyl;

(c) 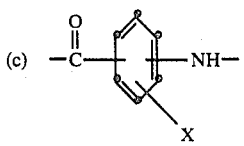

wherein X is hydrogen chloro, bromo, iodo, nitro, $C_1$-$C_3$ alkyl, hydroxy, $C_1$-$C_3$ alkoxy, mercapto, $C_1$-$C_3$ alkylthio, carbamyl, or $C_1$-$C_3$ alkylcarbamyl;

(d) 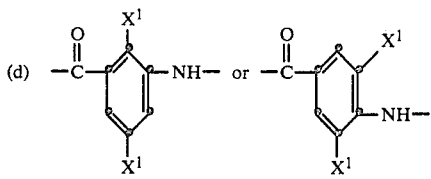

wherein $X^1$ is chloro, bromo, or iodo;

(e) 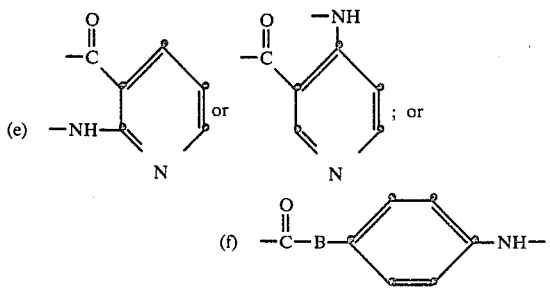

(f) 

wherein B is a divalent radical of the formula: $-(CH_2)_n-$, wherein n is an integer from 1 to 3; $-CH=CH-$; $-CH=CH-CH_2-$; or $$-\overset{O}{\underset{\|}{C}}NHCH_2-$$

and $R^2$ is $C_1$-$C_{17}$ alkyl or $C_2$-$C_{17}$ alkenyl.

As employed herein the terms "alkylene", "alkyl", "alkoxy", "alkylthio", and "alkenyl" comprehend both straight and branched hydrocarbon chains. "Alkyl" means a univalent saturated hydrocarbon radical. "Alkenyl" means a univalent unsaturated hydrocarbon radical containing one, two, or three double bonds, which may be oriented in the cis or trans configuration. "Alkylene" means a divalent saturated hydrocarbon radical. "Cycloalkylene" means a divalent cyclic saturated hydrocarbon radical.

Illustrative $C_1$-$C_{10}$ alkylene radicals, which are preferred for purposes of this invention are:
$-CH_2-$;

in which $R^5$ is $C_1$-$C_4$ alkyl (i.e., methyl, ethyl, n-propyl, i-propyl, n-butyl, t-butyl, i-butyl, or 1-methyl-propyl); $-(CH_2)_{\overline{m}}$ in which m is an integer from 2 to 10; and

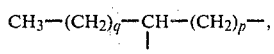

in which p is an integer from 1 to 8 and q is an integer from 0 to 7, provided that n+m must be no greater than 8.

Illustrative $C_1$-$C_{17}$ alkyl groups which are preferred for the purposes of this invention are:
(a) $CH_3-$;
(b) $-(CH_2)_nCH_3$ wherein n is an integer from 1 to 16; and (c) 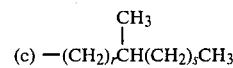

wherein r and s are independently, an integer from 0 to 14 provided that r+s can be no greater than 14.

Illustrative $C_2$-$C_{17}$ alkenyl radicals, which are preferred for the purpose of this invention, are
(a) $-(CH_2)_t-CH=CH-(CH_2)_u-CH_3$ wherein t and u are independently, an integer from 0 to 14 provided that t+u can be no greater than 14.
(b) $-(CH_2)_v-CH=CH-(CH_2)_y-CH=CH-(CH_2)_z-CH_3$ wherein v and z are independently, an integer from 0 to 11 and y is an integer from 1 to 12 provided that v+y+z can be no greater than 11.

In particular, the following embodiments of the $C_1$-$C_{17}$ alkyl groups are preferred:
$CH_3-$
$CH_3(CH_2)_5-$
$CH_3(CH_2)_6-$
$CH_3(CH_2)_8-$
$CH_3(CH_2)_{10}-$
$CH_3(CH_2)_{12}-$
$CH_3(CH_2)_{14}-$
$CH_3(CH_2)_{16}-$ In particular, the following embodiments of the $C_2$-$C_{17}$ alkenyl groups are preferred:
cis-$CH_3(CH_2)_5CH=CH(CH_2)_7-$
trans-$CH_3(CH_2)_5CH=CH(CH_2)_7-$
cis-$CH_3(CH_2)_{10}CH=CH(CH_2)_4-$
trans-$CH_3(CH_2)_{10}CH=CH(CH_2)_4-$
cis-$CH_3(CH_2)_7CH=CH(CH_2)_7-$
trans-$CH_3(CH_2)_7CH=CH(CH_2)_7-$
cis-$CH_3(CH_2)_5CH=CH(CH_2)_9-$
trans-$CH_3(CH_2)_5CH=CH(CH_2)_9-$
cis, cis-$CH_3(CH_2)_4CH=CHCH_2CH=CH(CH_2)_7-$
trans, trans-$CH_3(CH_2)_4CH=CHCH_2CH=CH(CH_2)_7-$
cis,cis,cis-$CH_3CH_2CH=CHCH_2CH=CHCH_2CH=CH-(CH_2)_7-$.

When "W" is a divalent radical of the formula

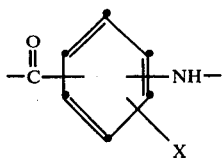

it will be recognized by those skilled in the art that the

function and the —NH— function may be oriented on the benzene ring in the ortho, meta, or para configuration relative to each other. The substituent represented by X may be substituted at any available position of the benzene ring. Preferred embodiments are those in which X is hydrogen and the

and —NH— functions are oriented in the para configuration.

The terms "substituted phenyl" and "substituted benzyl", as defined by $R_3$ in Formula III, contemplate substitution of a group at any of the available positions in the benzene ring—i.e. the substituent may be in the ortho, meta, or para configuration. The term "$C_1$–$C_3$ alkyl" as defined by $R_3$ or X in Formula III includes the methyl, ethyl, n-propyl, or i-propyl groups.

DETAILED DESCRIPTION OF THE INVENTION

The compounds of Formula III inhibit the growth of pathogenic fungi as evidenced by standard biological test procedures. The compounds are useful, therefore, for controlling the growth of fungi on environmental surfaces (as an antiseptic) or in treating infections caused by fungi. The antifungal activity of the compounds has been demonstrated against *Candida albicans* in vitro in agar plate disc diffusion tests and in agar dilution tests, or in vivo in tests in mice infected with *C. albicans*. Thus, the compounds are particularly useful in treating infections caused by strains of *C. albicans* (candidosis). The compounds of Formula III have also shown activity in vitro in agar-plate disc diffusion tests against *Trichophyton mentagrophytes*, a dermatophytic organism. Activity has also been found in in vitro agar plate disc diffusion tests against *Saccharomyces pastorianus*, and *Neurospora crassa*. Certain compounds (as shown in Example 92, Table 8) give significant blood levels upon oral administration in mice.

When given to a dog by intravenous administration, 100 mg/kg per day for five days, the compound of Formula III wherein R is n-dodecanoyl-p-aminobenzoyl showed no outward signs of toxicity, although increased SGPT levels were observed.

The compounds of Formula III are prepared by acylating A-30912A nucleus at the α-amino group of dihydroxyornithine with the appropriate N-alkanoyl aminoacyl or N-alkenoyl amino acyl side chain using methods conventional in the art for forming an amide bond. The acylation is accomplished, in general, by reacting the nucleus with an activated derivative of the acid (Formula IV) corresponding to the desired acyl side chain group.

(W and $R^2$ have the meaning described herein supra). By the term "activated derivative" is meant a derivative which renders the carboxyl function of the acylating agent reactive to coupling with the primary amino group to form the amide bond which links the acyl side chain to the nucleus. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, a N-hydroxybenztriazole ester, or an N-hydroxysuccinimide ester). Other methods for activating the carboxyl function include reaction of the carboxylic acid with a carbonyldiimide (e.g. N,N-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of Formula III is by the active ester method. The use of the 2,4,5-trichlorophenyl ester of the desired N-alkanoylamino acid or N-alkenoylamino acid (Formula IV) as the acylating agent is most preferred. In this method, an excess amount of the active ester is reacted with the nucleus at room temperature in a nonreactive organic solvent such as dimethyl formamide (DMF). The reaction time is not critical, although a time of about 15 to about 18 hours is preferred. At the conclusion of the reaction, the solvent is removed, and the residue is purified such as by column chromatography using silica gel as the stationary phase and a mixture of ethyl acetate/methanol (3:2, v/v) as the solvent system.

The 2,4,5-trichlorophenyl esters of the N-alkanoylamino acids or N-alkenoylamino acids can be prepared conveniently by treating the desired amino acid (Formula IV) with 2,4,5-trichlorophenol in the presence of a coupling agent, such as N,N'-dicyclohexylcarbodiimide. Other methods suitable for preparing amino acid esters will be apparent to those skilled in the art.

The N-alkanoylamino acids or N-alkenoylamino acids are either known compounds or they can be made by acylating the appropriate amino acid with the appropriate alkanoyl or alkenoyl group using conventional methods, such as those described herein supra. A preferred way of preparing the N-alkanoylamino acids is by treating the appropriate amino acid with an alkanoic acid chloride in pyridine. The alkanoic acids or alkenoic acids, the activated derivatives thereof, and the amino acids employed in the preparation of the products of this invention are either known compounds or they can be made by known methods or by modification of known methods which will be apparent to those skilled in the art.

If a particular amino acid contains an acylable functional group other than the amino group, it will be understood by those skilled in the art that such a group must be protected prior to reaction of the amino acid with the reagent employed to attach the alkanoyl or alkenoyl group. Suitable protecting groups can be any group known in the art to be useful for the protection of a side chain functional group in peptide synthesis. Such groups are well known, and the selection of a particular protecting group and its method of use will be readily known to one skilled in the art [see, for example, "Protective Groups In Organic Chemistry", M. McOmie, Editor, Plenum Press, N.Y., 1973].

It will be recognized that certain amino acids employed in the synthesis of the products of this invention may exist in optically active forms, and both the natural configuration (L-configuration) and unnatural configuration (D-configuration) may be employed as starting materials and will give products which are within the contemplation of this invention.

When employed systemically, the dosage of the compounds of Formula III will vary according to the particular compound being employed, the severity and nature of the infection, and the physical condition of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

Certain compounds of Formula III give significant blood levels after oral administration (see Example 92, Table 8) and can be administered systemically by the oral route. For oral use, such compounds can be administered in combination with pharmaceutically acceptable carriers or excipients in the form of capsules, tablets or powders. The nature and proportion of such carriers or excipients of which will be recognized by those skilled in the art.

When employed to treat vaginal candida infections, the compounds of Formula III can be administered in combination with pharmaceutically acceptable conventional excipients suitable for intravaginal use. Formulations adapted for intravaginal administration will be known to those skilled in the art.

The methods of making and using the compounds of the present invention are illustrated in the following examples

EXAMPLES 1-30

Table 1, below, gives the preparation of various N-alkanoyl amino acids. The compounds shown in Table 1 are prepared according to the following general procedure:

The appropriate alkanoic acid chloride is added dropwise to the appropriate amino acid (1:1 mole ratio) dissolved in pyridine. The amount of pyridine employed should be such as to make the concentration of reactants between 0.1 to 0.2 M. The solution is stirred at room temperature for about 3 to 6 hours, after which it is poured into a large volume of water. The product precipitates from solution and is collected by filtration and crystallized from methanol.

TABLE 1

Preparation of N-alkanoyl Amino Acids

| Example No. | Alkanoic acid chloride Formula | wt. | Amino Acid Formula | wt. |
|---|---|---|---|---|
| 1 | $CH_3(CH_2)_{10}COCl$ | 3.00 g | $NH_2CH(CH_2C_6H_5)CO_2H$ | 2.0 g. |
| 2 | $CH_3(CH_2)_{10}COCl$ | 234 mg | $NH_2(CH)_4CO_2H$ | 482 mg. |
| 3 | $CH_3(CH_2)_{10}COCl$ | 21.85 g. | $NH_2(CH_2)_{10}CO_2H$ | 20.1 mg. |
| 4 | $CH_3(CH_2)_{10}COCl$ | 11.09 g. | 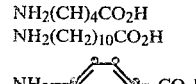 | 6.2 g. |
| 5 | $CH_3(CH_2)_{10}COCl$ | 2.19 g. | 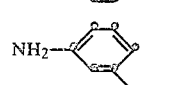 | 1.37 g. |
| 6 | $CH_3(CH_2)_{10}COCl$ | 437 mg. | 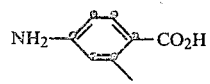 | 306 mg. |
| 7 | $CH_3(CH_2)_{10}COCl$ | 2.17 g. | 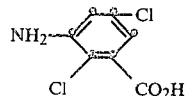 | 2.06 g. |
| 8 | $CH_3(CH_2)_{10}COCl$ | 2.17 g. | 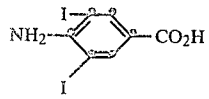 | 3.89 g. |

TABLE 1-continued

Preparation of N-alkanoyl Amino Acids

| # | Acyl chloride | Amount | Amino acid | Product |
|---|---|---|---|---|
| 9 | $CH_3(CH_2)_{10}COCl$ | 2.17 g. | 3-amino-4-methylbenzoic acid ($CH_3$, $NH_2$ on ring, $CO_2H$) | 1.51 g. |
| 10 | $CH_3(CH_2)_{10}COCl$ | 2.17 g. | 4-amino-3-methylbenzoic acid ($NH_2$, $CO_2H$ on ring, $CH_3$) | 1.51 g. |
| 11 | $CH_3(CH_2)_{10}COCl$ | 2.17 g. | 3-methoxy-4-aminobenzoic acid ($CH_3O$, $NH_2$, $CO_2H$) | 1.67 g. |
| 12 | $CH_3(CH_2)_{10}COCl$ | 21.85 g. | $NH_2$—C$_6$H$_4$—$CH_2CO_2H$ | 15.1 g. |
| 13 | $CH_3(CH_2)_{10}COCl$ | 2.19 g. | $NH_2$—C$_6$H$_4$—$CH=CH-CO_2H$ | 1.6 g. |
| 14 | $CH_3(CH_2)_{10}COCl$ | 21.85 g. | $NH_2$—C$_6$H$_4$—$CONHCH_2CO_2H$ | 19.4 g. |
| 15 | $CH_3(CH_2)_{10}COCl$ | 8.52 g. | 3-amino-2-pyridinecarboxylic acid ($HO_2C$, $NH_2$, N on ring) | 5.4 g. |
| 16 | $CH_3(CH_2)_5COCl$ | 14.85 g. | $NH_2(CH_2)_{10}CO_2H$ | 20.1 g. |
| 17 | $CH_3COCl$ | 785 mg. | $NH_2$—C$_6$H$_4$—$CO_2H$ | 1.37 g. |
| 18 | $CH_3(CH_2)_5COCl$ | 1.49 g. | $NH_2$—C$_6$H$_4$—$CO_2H$ | 1.37 g. |
| 19 | $CH_3(CH_2)_8COCl$ | 1.91 g. | $NH_2$—C$_6$H$_4$—$CO_2H$ | 1.37 g. |
| 20 | $CH_3(CH_2)_{12}COCl$ | 2.46 g. | $NH_2$—C$_6$H$_4$—$CO_2H$ | 1.37 g. |
| 21 | $CH_3(CH_2)_{14}COCl$ | 2.74 g. | $NH_2$—C$_6$H$_4$—$CO_2H$ | 1.37 g. |
| 22 | $CH_3(CH_2)_6COCl$ | 3.42 g. | Cl, $CO_2H$, $NH_2$-substituted benzene | 3.43 g. |
| 23 | $CH_3(CH_2)_{10}COCl$ | 4.60 g. | Cl, $CO_2H$, $NH_2$-substituted benzene | 3.43 g. |
| 24 | $CH_3(CH_2)_6COCl$ | 3.42 g. | Cl—C$_6$H$_3$($NH_2$)—$CH_2H$ | 3.43 g. |
| 25 | $CH_3(CH_2)_{10}COCl$ | 4.60 g. | Cl—C$_6$H$_3$($NH_2$)—$CO_2H$ | 3.43 g. |
| 26 | $CH_3(CH_2)_6COCl$ | 3.42 g. | Cl, $NH_2$, $CO_2H$-substituted benzene | 3.43 g. |
| 27 | $CH_3(CH_2)_{10}COCl$ | 4.60 g. | Cl, $NH_2$, $CO_2H$-substituted benzene | 3.43 g. |

TABLE 1-continued

| | Preparation of N-alkanoyl Amino Acids | | | |
|---|---|---|---|---|
| 28 | CH$_3$(CH$_2$)$_6$COCl | 3.42 g. | Cl, NH$_2$, Cl, CO$_2$H (benzene ring) | 6.18 g. |
| 29 | CH$_3$(CH$_2$)$_8$COCl | 4.01 g. | Cl, NH$_2$, Cl, CO$_2$H (benzene ring) | 4.12 g. |
| 30 | CH$_3$(CH$_2$)$_{12}$COCl | 5.18 g. | Cl, NH$_2$, Cl, CO$_2$H (benzene ring) | 4.12 g. |

| Example No. | N-Alkanoyl Amino Acid Formula | wt. |
|---|---|---|
| 1 | CH$_3$(CH$_2$)$_{10}$CONHCH(C$_5$H$_5$)CO$_2$H | 2.5 g. |
| 2 | CH$_3$(CH$_2$)$_{10}$CONH(CH$_2$)$_4$CO$_2$H | 598 mg. |
| 3 | CH$_3$(CH$_2$)$_{10}$CONH(CH$_2$)$_{10}$CO$_2$H | 19.97 g. |
| 4 | CH$_3$(CH$_2$)$_{10}$CONH—⟨C$_6$H$_4$⟩—CO$_2$H | 6.0 g. |
| 5 | CH$_3$(CH$_2$)$_{10}$CONH—⟨C$_6$H$_4$⟩—CO$_2$H (meta) | 3.19 g. |
| 6 | CH$_3$(CH$_2$)$_{10}$CONH—⟨C$_6$H$_3$(OH)⟩—CO$_2$H | 670 mg. |
| 7 | CH$_3$(CH$_2$)$_{10}$CONH—⟨C$_6$H$_2$Cl$_2$⟩—CO$_2$H | 3.58 g. |
| 8 | CH$_3$(CH$_2$)$_{10}$CONH—⟨C$_6$H$_2$I$_2$⟩—CO$_2$H | 5.23 g. |
| 9 | CH$_3$(CH$_2$)$_{10}$CONH—⟨C$_6$H$_3$(CH$_3$)⟩—CO$_2$H | 3.04 g. |
| 10 | CH$_3$(CH$_2$)$_{10}$CONH—⟨C$_6$H$_3$(CH$_3$)⟩—CO$_2$H | 2.87 |
| 11 | CH$_3$(CH$_2$)$_{10}$CONH—⟨C$_6$H$_3$(OCH$_3$)⟩—CO$_2$H | 3.34 g. |
| 12 | CH$_3$(CH$_2$)$_{10}$CONH—⟨C$_6$H$_4$⟩—CH$_2$CO$_2$H | 33.3 g. |
| 13 | CH$_3$(CH$_2$)$_{10}$CONH—⟨C$_6$H$_4$⟩—CH=CH—CO$_2$H | 2.76 g. |
| 14 | CH$_3$(CH$_2$)$_{10}$CONH—⟨C$_6$H$_4$⟩—CONHCH$_2$CO$_2$H | 37.6 g. |
| 15 | CH$_3$(CH$_2$)$_{10}$CONH—⟨pyridine⟩—CO$_2$H | 7.6 g. |
| 16 | CH$_3$(CH$_2$)$_5$CONH(CH$_2$)$_{10}$CO$_2$H | 31.3 g. |
| 17 | CH$_3$CONH—⟨C$_6$H$_4$⟩—CO$_2$H | 1.56 g. |

TABLE 1-continued
Preparation of N-alkanoyl Amino Acids

| | | |
|---|---|---|
| 18 | $CH_3(CH_2)_5CONH\text{—}C_6H_3\text{—}CO_2H$ | 2.25 g. |
| 19 | $CH_3(CH_2)_8CONH\text{—}C_6H_3\text{—}CO_2H$ | 2.52 g. |
| 20 | $CH_3(CH_2)_{12}CONH\text{—}C_6H_3\text{—}CO_2H$ | 2.84 g. |
| 21 | $CH_3(CH_2)_{14}CONH\text{—}C_6H_3\text{—}CO_2H$ | 3.16 g. |
| 22 | 3-Cl, 4-$NHCO(CH_2)_6CH_3$ benzoic acid | 3.20 g. |
| 23 | 3-Cl, 4-$NHCO(CH_2)_{10}CH_3$ benzoic acid | 2.89 g. |
| 24 | 3-Cl, 4-$NHCO(CH_2)_6CH_3$ benzoic acid (isomer) | 3.19 g. |
| 25 | 3-Cl, 4-$NHCO(CH_2)_{10}CH_3$ benzoic acid (isomer) | 4.26 g. |
| 26 | $CH_3(CH_2)_6CONH$—(Cl-substituted benzoic acid) | 4.76 g. |
| 27 | $CH_3(CH_2)_{10}CONH$—(Cl-substituted benzoic acid) | 6.23 g. |
| 28 | 3,5-diCl, 4-$NHCO(CH_2)_6CH_3$ benzoic acid | 4.26 g. |
| 29 | 3,5-diCl, 4-$NHCO(CH_2)_8CH_3$ benzoic acid | 3.638 g. |
| 30 | 3,5-diCl, 4-$NHCO(CH_2)_{12}CH_3$ benzoic acid | 4.187 g. |

EXAMPLES 31-60

Table 2, below, gives the preparation of the 2,4,5-trichlorophenyl esters of the N-alkanoyl amino acids shown in Table 1. The compounds set forth in Table 2 are prepared according to the following general procedure:

The N-alkanoylamino acid (1 mole), 2,4,5-trichlorophenol (1.1 mole), and dicyclohexylcarbodiimide (1 mole) are dissolved in methylene chloride, ether or tetrahydrofuran. The solution is stirred at room temperature for about 16 to about 20 hours after which it is filtered. The filtrate is taken to dryness, and the product is crystallized from either acetonitrilewater or diethyl ether-petroleum ether.

TABLE 2

| | Preparation of 2,4,5-trichlorophenyl esters | | Wt. of 2,4,5-trichlorophenol |
|---|---|---|---|
| | N-Alkanoyl Amino Acid | | |
| Example No. | Formula | wt | ester product |
| 31 | $CH_3(CH_2)_{10}CONHCH(CH_2C_6H_5)CO_2H$ | 333 mg. | 500 mg. |
| 32 | $CH_3(CH_2)_{10}CONH(CH_2)_4CO_2H$ | 598 mg. | 955 mg |
| 33 | $CH_3(CH_2)_{10}CONH(CH_2)_{10}CO_2H$ | 3.83 g. | 1.02 g. |
| 34 | $CH_3(CH_2)_{10}CONH$—⌬—$CO_2H$ | 638 mg. | 410 mg. |
| 35 | $CH_3(CH_2)_{10}CONH$—⌬—$CO_2H$ (meta) | 3.19 g. | 2.43 g. |
| 36 | $CH_3(CH_2)_{10}CONH$—⌬—$CO_2H$, OH | 670 mg. | 1.03 g. |
| 37 | $CH_3(CH_2)_{10}CONH$—⌬(Cl, Cl)—$CO_2H$ | 3.58 g. | 2.20 g. |
| 38 | $CH_3(CH_2)_{10}CONH$—⌬(I, I)—$CO_2H$ | 5.23 g. | 1.41 g. |
| 39 | $CH_3(CH_2)_{10}CONH$—⌬($CH_3$)—$CO_2H$ | 3.04 g. | 4.7 g. |
| 40 | $CH_3(CH_2)_{10}CONH$—⌬($CH_3$)—$CO_2H$ | 2.87 g. | 4.45 g. |
| 41 | $CH_3(CH_2)_{10}CONH$—⌬($CH_3O$)—$CO_2H$ | 3.34 g. | 3.86 g. |
| 42 | $CH_3(CH_2)_{10}CONH$—⌬—$CH_2CO_2H$ | 3.33 g. | 2.6 g. |
| 43 | $CH_3(CH_2)_{10}CONH$—⌬—$CH=CH-CO_2H$ | 2.76 g. | 2.14 g. |
| 44 | $CH_3(CH_2)_{10}CONH$—⌬—$CONHCH_2CO_2H$ | 3.76 g. | 1.0 g. |
| 45 | $CH_3(CH_2)_{10}CONH$—pyridyl—$HO_2C$ | 3.28 g. | 4.4 g. |
| 46 | $CH_3(CH_2)_5CONH(CH_2)_{10}CO_2H$ | 4.8 g. | 1.68 g. |
| 47 | $CH_3CONH$—⌬—$CO_2H$ | 895 mg. | 1.48 g. |
| 48 | $CH_3(CH_2)_5$—$CONH$—⌬—$CO_2H$ | 1.245 g. | 1.59 g. |
| 49 | $CH_3(CH_2)_8CONH$—⌬—$CO_2H$ | 2.52 g. | 2.97 g. |
| 50 | $CH_3(CH_2)_{12}CONH$—⌬—$CO_2H$ | 2.84 g. | 2.44 g. |
| 51 | $CH_3(CH_2)_{14}CONH$—⌬—$CO_2H$ | 3.16 g. | 1.33 g. |
| 52 | ⌬(Cl)—$CO_2H$, $NHCO(CH_2)_6CH_3$ | 2.08 g. | 2.436 g. (700 mg. after recryst.) |

TABLE 2-continued

| | Preparation of 2,4,5-trichlorophenyl esters | | Wt. of 2,4,5-trichlorophenol |
|---|---|---|---|
| | N-Alkanoyl Amino Acid | | |
| Example No. | Formula | wt | ester product |
| 53 | 2-Cl, 1-$CO_2H$, 6-$NHCO(CH_2)_{10}CH_3$ phenyl | 2.65 g. | 2.373 g. |
| 54 | 4-Cl, 1-$CO_2H$, 2-$NHCO(CH_2)_6CH_3$ phenyl | 2.68 g. | 1.619 g. |
| 55 | 4-Cl, 1-$CO_2H$, 2-$NHCO(CH_2)_{10}CH_3$ phenyl | 3.19 g. | 1.605 g. |
| 56 | 2-Cl, 1-$CO_2H$, 4-$CH_3(CH_2)_6CONH$ phenyl | 2.38 g. | 1.716 g. |
| 57 | 2-Cl, 1-$CO_2H$, 4-$CH_3(CH_2)_{10}CONH$ phenyl | 2.83 g. | 1.575 g. |
| 58 | 2,6-diCl, 1-$CO_2H$, 3-$NHCO(CH_2)_6CH_3$ phenyl | 4.19 g. | 2.02 g. |
| 59 | 2,6-diCl, 1-$CO_2H$, 3-$NHCO(CH_2)_8CH_3$ phenyl | 2.88 g. | 3.507 g. |
| 60 | 2,6-diCl, 1-$CO_2H$, 3-$NHCO(CH_2)_{12}CH_3$ phenyl | 3.33 g. | 1.897 g. |

EXAMPLES 61–90

Table 3, below, gives the preparation of the derivatives of A-30912A nucleus prepared from the N-alkanoyl amino acid 2,4,5-trichlorophenyl esters set forth in Table 2. The compounds set forth in Table 3 are prepared in general according to the following procedure:

To A-30912A nucleus, dissolved in dimethylformamide (DMF) is added the 2,4,5-trichlorophenyl ester of the N-alkanoyl amino acid. The reaction mixture is stirred for 15–18 hours after which it is taken to dryness to give a residue. The residue is washed (two times each) with ethyl ether and by methylene chloride. The washings are discarded. The remaining residue is dissolved in ethyl acetate-methanol (3:2, v/v) and is chromatographed on a silica gel (Woelm 70-150 mesh) column using the aforesaid solvent system as the eluent. The fractions from the chromatograph are monitored by TLC on silica gel (Merck) using ethyl acetate-methanol (3:2, v/v) as the solvent system. Fractions containing the desired product are combined, and solvent is removed to give the product as a residue. The product may be analyzed by reversed phase HPLC as follows: The sample dissolved in $H_2O$/$CH_3OH$/$CH_3CN$ (1:2:2 v/v)(1 mg./ml.) is injected into a ¼ inch by 12 inch stainless steel column packed with $C_{18}$ Micro Bondapak resin (Waters Associates, Inc., Milford, Mass) and the column is eluted with a solvent system comprising $H_2O$/$CH_3OH$/$CH_3CN$ (1:2:2 v/v). The elution is performed at a pressure of 1500 psi with a flow rate of 3 ml./minute using a Waters 600A pump (Waters Associates, Inc.) and chart speed of 0.2 in./minute. Eluent is monitored with a Varian Vari-Chrom UV detector at 230 nm.

The products may also be analyzed by field desorption mass spectrometry (FDMS).

TABLE 3

N-Alkanoylamino Acid Derivatives of A-30912A Nucleus

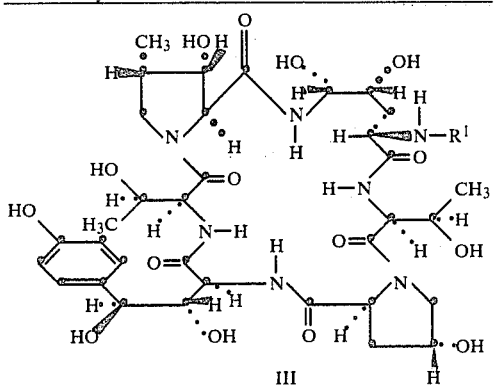

III

| Example No. | Product $R^1$ in Formula III | Ester Example | Ester Wt. (mg) | A30912A nucleus (mg) | Product (mg) | $M^+$ | HPLC Retention (cm) |
|---|---|---|---|---|---|---|---|
| 61 | $CH_3(CH_2)_{10}CONHCH(CH_2C_6H_5)CO-$ | 31 | 141 | 250 | 158 | 1148($M^+$ + 22) | — |
| 62 | $CH_3(CH_2)_{10}CONH(CH_2)_4-CO-$ | 32 | 795 | 250 | 132 | 1101($M^+$ + 22) | — |
| 63 | $CH_3(CH_2)_{10}CONH(CH_2)_{10}-CO-$ | 33 | 462 | 400 | 327 | 1185($M^+$ + 23) | 1.23 |
| 64 | $CH_3(CH_2)_{10}CONH-\langle\text{phenyl}\rangle-CO-$ | 34 | 515 | 400 | 247 | 1121($M^+$ + 23) | — |
| 65 | $CH_3(CH_2)_{10}CONH-\langle\text{phenyl}\rangle-CO-$ | 35 | 515 | 400 | 302 | 1120($M^+$ + 22) | — |
| 66 | $CH_3(CH_2)_{10}CONH-\langle\text{phenyl-OH}\rangle-CO-$ | 36 | 515 | 400 | 354 | 1137($M^+$ + 23) | 1.33 |
| 67 | $CH_3(CH_2)_{10}CONH-\langle\text{phenyl-Cl}_2\rangle-CO-$ | 37 | 570 | 400 | 196 | 1197($M^+$ + 30) | 1.65 |
| 68 | $CH_3(CH_2)_{10}CONH-\langle\text{phenyl-I}_2\rangle-CO-$ | 38 | 750 | 400 | 291 | — | 1.20 |
| 69 | $CH_3(CH_2)_{10}CONH-\langle\text{phenyl-CH}_3\rangle-CO-$ | 39 | 512 | 400 | 182 | 1135($M^+$ + 23) | — |
| 70 | $CH_3(CH_2)_{10}CONH-\langle\text{phenyl-CH}_3\rangle-CO-$ | 40 | 512 | 400 | 166 | 1143($M^+$ + 31) | 1.43 |
| 71 | $CH_3(CH_2)_{10}CONH-\langle\text{phenyl-OCH}_3\rangle-CO-$ | 41 | 530 | 400 | 120 | 1151($M^+$ + 23) | — |
| 72 | $CH_3(CH_2)_{10}CONH-\langle\text{phenyl}\rangle-CH_2CO-$ | 42 | 497 | 400 | 452 | 1135($M^+$ + 23) | 1.32 |
| 73 | $CH_3(CH_2)_{10}CONH-\langle\text{phenyl}\rangle-CH=CH-CO-$ | 43 | 535 | 400 | 286 | 1148($M^+$ + 24) | 1.40 |
| 74 | $CH_3(CH_2)_{10}CONH-\langle\text{phenyl}\rangle-CONHCH_2-CO-$ | 44 | 540 | 400 | 453 | 1170($M^+$ + 25) | 1.40 |
| 75 | $CH_3(CH_2)_{10}CONH-\langle\text{pyridyl}\rangle-CO-$ | 45 | 492 | 400 | 277 | — | — |
| 76 | $CH_3(CH_2)_5CONH(CH_2)_{10}-CO-$ | 46 | 493 | 400 | 273 | 1115($M^+$ + 23) | 0.95 |
| 77 | $CH_3CONH-\langle\text{phenyl}\rangle-CO-$ | 47 | 360 | 400 | 213 | 980($M^+$ + 22) | 1.75 |

TABLE 3-continued

N-Alkanoylamino Acid Derivatives of A-30912A Nucleus

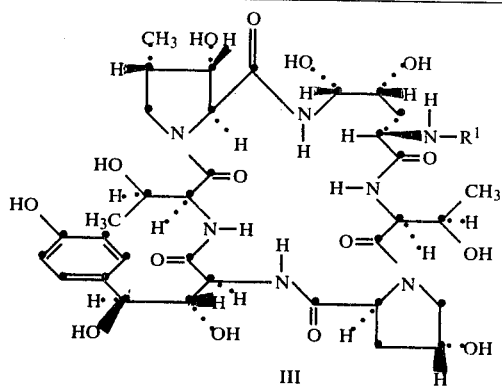

III

| Example No. | Product R¹ in Formula III | Ester Example | Wt. (mg) | A30912A nucleus (mg) | Product (mg) | $M^+$ | HPLC Retention (cm) |
|---|---|---|---|---|---|---|---|
| 78 | $CH_3(CH_2)_5$—CONH—⟨ ⟩—CO— | 48 | 430 | 400 | 218 | — | — |
| 79 | $CH_3(CH_2)_8$CONH—⟨ ⟩—CO— | 49 | 500 | 400 | 162 | 1093($M^+$ + 23) | 0.90 |
| 80 | $CH_3(CH_2)_{12}$CONH—⟨ ⟩—CO— | 50 | 527 | 400 | 234 | 1149($M^+$ + 23) | 2.35 |
| 81 | $CH_3(CH_2)_{14}$CONH—⟨ ⟩—CO— | 51 | 555 | 400 | 350 | 1177($M^+$ + 23) | 3.23 |
| 82 | Cl / CO— / NHCO(CH_2)_6CH_3 | 52 | 477 | 400 | 176 | 1099($M^+$ + 23) | 0.7 |
| 83 | Cl / CO— / NHCO(CH_2)_{10}CH_3 | 53 | 533 | 400 | 127 | 1155($M^+$ + 23) | 2.3 |
| 84 | Cl—⟨ ⟩—CO— / NHCO(CH_2)_6CH_3 | 54 | 477 | 400 | 319 | 1099($M^+$ + 23) | 1.0 |
| 85 | Cl—⟨ ⟩—CO— / NHCO(CH_2)_{10}CH_3 | 55 | 533 | 400 | 214 | 1155($M^+$ + 23) | 3.1 |
| 86 | $CH_3(CH_2)_6$CONH—⟨ ⟩—CO— (Cl) | 56 | 477 | 400 | 290 | | 1.0 |
| 87 | $CH_3(CH_2)_{10}$CONH—⟨ ⟩—CO— (Cl) | 57 | 533 | 400 | 325 | | 3.4 |
| 88 | Cl, Cl / CO— / NHCO(CH_2)_6CH_3 | 58 | 512 | 400 | 324 | | 1.3 |
| 89 | Cl, Cl / CO— / NHCO(CH_2)_8CH_3 | 59 | 540 | 400 | 281 | 1162($M^+$ + 23) | 1.8 |

TABLE 3-continued
N-Alkanoylamino Acid Derivatives of A-30912A Nucleus

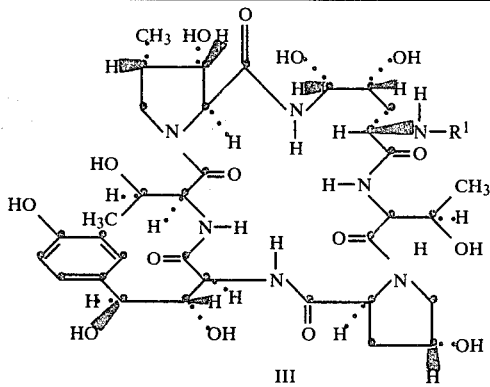

III

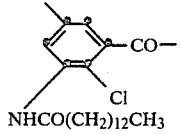

| Example No. | Product $R^1$ in Formula III | Ester Example | Wt. (mg) | A30912A nucleus (mg) | Product (mg) | $M^+$ | HPLC Retention (cm) |
|---|---|---|---|---|---|---|---|
| 90 | (structure with Cl, Cl, CO—, NHCO(CH₂)₁₂CH₃) | 60 | 596 | 400 | 269 | $1217(M^+ + 23)$ | 7.7 |

EXAMPLE 91

The following procedure illustrates the larger-scale preparation of the compounds of Formula III. The specific compound prepared by the procedure given below is the compound of Formula III wherein $R^1$ is N-(n-dodecanoyl)-p-aminobenzoyl.

A. Preparation of N-(n-Dodecanoyl)-p-aminobenzoic acid n-dodecanoyl chloride (8.74 g.; 40 mmoles) is added dropwise to a solution of dissolved p-aminobenzoic acid (5.5 g.; 40 mmoles) dissolved in pyridine (100 ml.). The mixture is stirred for 3 hours and poured into water (3 l.). The precipitate which forms is filtered and dried in vacuo to give N-(n-dodecanoyl)-p-aminobenzoic acid (11.01 g.).

B. Preparation of the 2,4,5-trichlorophenyl ester of N-(n-dodecanoyl)-p-aminobenzoic acid N-(n-Dodecanoyl)-p-aminobenzoic acid (11.01 g.; 34.5 mmole), 2,4,5-trichlorophenol (7.5 g.; 38 mmole), and dicyclohexylcarbodiimide (6.94 g.; 34.5 mmole) are dissolved in methylene chloride (250 ml). The mixture is stirred at room temperature for 3.5 hours and then filtered. The filtrate is evaporated in vacuo to give a residue which is crystallized from acetonitrile/water to afford the 2,4,5-trichlorophenyl ester of N-(n-dodecanoyl)-p-aminobenzoic acid (12.84 g.).

C. Acylation of A-30912A nucleus

A-30912A nucleus (8.16 g.; 10.2 mmole) and the 2,4,5-trichlorophenyl ester of N-(n-dodecanoyl)-p-aminobenzoic acid (4.72 g.; 10.2 mmole) are dissolved in dimethylformamide (100 ml.). The solution is stirred at room temperature for 15 hours. Solvent is removed in vacuo to give a residue which is washed twice with diethylether. The washes are discarded. The washed residue is dissolved in methanol (50 ml.) and is purified by reversed phase HPLC by means of a "Prep LC/System 500" unit (Waters Associates, Inc., Milford, Mass.) using a Prep Pak-500/$C_{18}$ Column (Waters Associates, Inc.) as the stationary phase. The column is eluted isocratically with $H_2O/CH_3OH/CH_3CN$ (25:65:10 v/v) at 500 psi. The fractions are analyzed by TLC using silica gel plates and $H_2O/CH_3OH/CH_3CN$ (25:65:10 v/v) as the solvent system. Fractions containing the desired product are combined and lyophilized to give the N-(n-dodecanoyl)-p-aminobenzoyl derivative of A-30912A nucleus (3.5 g).

EXAMPLE 92

The antifungal activity of the compounds of Formula III can be demonstrated and elicited in vitro in standard disc-diffusion tests and agar-dilution tests, and in vivo in standard tests in mice which assess effectiveness against a systemic fungal infection. The results of the antifungal testing of representative compounds of Formula III (Example 61–90) are set forth in Tables 4, 5, 6 and 7.

Tables 4 and 5 give the results of the testing in vitro of the compounds of Examples 61–81 by agar-plate disc-diffusion methods. In Table 4 activity is measured by the size (diameter in mm.) of the observed zone of inhibition of the microorganism produced by the test compound. In Table 5, activity is measured by the minimal inhibitory concentration (MIC) of the substance (µg/disc) required to inhibit growth of the test organism. Table 6 gives the results of the testing in vitro of the N-(n-dodecanoyl)-p-aminobenzoyl derivative of A30912A nucleus (Formula III, $R^1$ is N-(dodecanoyl)-p-aminobenzoyl) against five strains of *Candida albicans* by the agar dilution method. In Table 6 activity is measured by the minimal inhibitory concentration (MIC) of the substance (µg/ml) required to inhibit the test organism.

The results of in vivo tests to evaluate the effectiveness of the compound of Examples 61–81, 86 and 88 against an infection caused by *Candida albicans* A-26 in mice are given in Table 7, where activity is measured by the $ED_{50}$ value (the dose in mg/kg. required to cure 50% of the test animals). Where an $ED_{50}$ value was not obtained, activity is indicated by the lowest dose at which a significant anti-fungal effect is observed. In this test, groups of male albino mice (specific pathogen free), weighing 18 to 20 grams, are infected intravenously with *Candida albicans* A-26. The animals are X-irradiated 24 hours prior to infection at about 50 roentgens per minute for 8 minutes (400 total dose) to reduce immune responses to the infecting organism. At 0, 4, and 24 hours post infection each group of mice is given graded doses subcutaneously of the test compound as a suspension in 33% polyethylene glycol-water. The day of death for each animal is recorded. Student's t test statistical comparison of the average day of death is made between each group of infected-treated animals at a particular dosage level and 10 infected-untreated animals to determine if treatment significantly extends survival time.

Table 8 gives the results of the testing of compounds for absorption after oral administration. In this test, mice are gavaged with a dose of 416 mg/kg of the test compound suspended in 33% PEG 400-water. At time intervals, blood samples are taken from the orbital sinus and are assayed for antibiotic activity as follows: A 7 mm. disc containing 20 μl of whole blood is placed on agar seeded with *Aspergillus montevidensis* A35137. After 40 hours incubation at 30° C. zones of inhibition from the blood samples are compared to a standard obtained from the test compound, and the amount of compound in the blood sample is calculated.

TABLE 4

Antifungal Activity By the Agar Plate Disc Diffusion Test

| Example No. | $R^1$ of Formula III | *Saccharomyces pastorianus* X-52 | *Neurospora Crassa* 846 | *Trichophyton mentagrophytes* A-23 | *Candida albicans* A-26 |
|---|---|---|---|---|---|
| 61 | $CH_3(CH_2)_{10}CONHCH(CH_2C_6H_5)-CO-$ | 18 | 42* | 55* | 25 |
| 62 | $CH_3(CH_2)_{10}CONH(CH_2)_4-CO-$ | 15 | 27* | 60* | 25 |
| 63 | $CH_3(CH_2)_{10}CONH(CH_2)_{10}-CO-$ | 15 | 28* | 55* | 24 |
|  |  | 18 | 35 | 63* | 25 |
|  |  | 15 | 28 | 56 | 24 |
| 64 | 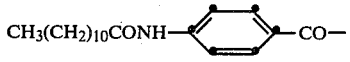 | 21 | 33* | 55* | 23 |
|  |  | 17 | 35* | 56* | 19 |
| 65 | 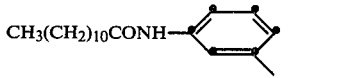 | 17 | — | — | 20 |
| 66 | 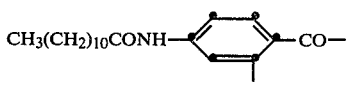 | 18 | — | — | 23 |
| 67 | 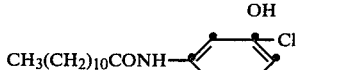 | 19 | 35* | 44* | 27 |
| 68 | 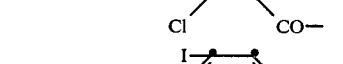 | 17 | 30* | 60 | 25 |
| 69 | 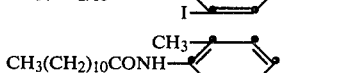 | 17 | 30* | — | 16 |
| 70 | 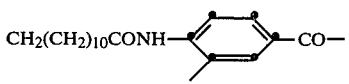 | 19 | 25* | 45* | 26 |
| 71 | 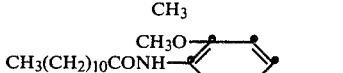 | 10 | 32* | 50* | 20 |
| 72 | 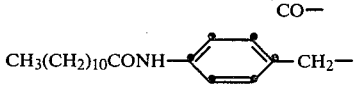 | 20 | 30* | 55* | 19 |
| 73 | 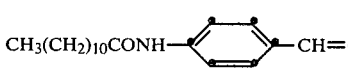 | 17 | 29* | 24* | 60* |
| 74 | 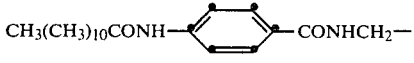 | 13 | 28* | — | 15 |

TABLE 4-continued

Antifungal Activity By the Agar Plate Disc Diffusion Test

| Compound | | Size of Zone of Inhibition (mm)[a] | | | |
|---|---|---|---|---|---|
| Example No. | $R^1$ of Formula III | Saccharomyces pastorianus X-52 | Neurospora Crassa 846 | Trichophyton mentagrophytes A-23 | Candida albicans A-26 |
| 75 | $CH_3(CH_2)_{10}CONH$-(pyridine ring)-CO— | 14 | 30* | 54* | 24 |
| 76 | $CH_3(CH_2)_5CONH(CH_2)_{10}$—CO— | — | 20* | 35* | 10 |
| 77 | $CH_3CONH$-(phenyl)-CO— | 17 | 24* | 51* | 24 |
| 78 | $CH_3(CH_2)_5CONH$-(phenyl)-CO— | 20 | 25 | 14 | 45* |
| 79 | $CH_3(CH_2)_8CONH$-(phenyl)-CO— | 17 | 30* | — | 24 |
| 80 | $CH_3(CH_2)_{12}CONH$-(phenyl)-CO— | 17 | — | — | 22 |
| 81 | $CH_3(CH_2)_{14}CONH$-(phenyl)-CO— | 24 | — | — | 25 |

[a] Compounds were tested as suspension in methanol. The compounds were tested at a concentration of 1 mg/ml by a dipping 7-mm disc into the suspension and placing it on the agar surface. Incubation: 24–48 hours at 25–37° C.
*Measurable zone of inhibition with regrowth of organism around disc.

TABLE 5

Antifungal Activity By the Agar Plate Disc Diffusion Test

| Compound | | MIC (μg/disc)* | |
|---|---|---|---|
| Example No. | $R^1$ or Formula III | Candida albicans A-26 | Trychophyton mentagrophytes #6 |
| 61 | $CH_3(CH_2)_{10}CONHCH(CH_2C_6H_5)$—CO— | 0.625 | <0.039 |
| 62 | $CH_3(CH_2)_{10}CONH(CH_2)_4$—CO— | 1.25 | 0.078 |
| 63 | $CH_3(CH_2)_{10}CONH(CH_2)_{10}$—CO— | 2.5 | 0.156 |
|  |  | 1.25 | 0.156 |
| 64 | $CH_3(CH_2)_{10}CONH$-(phenyl)-CO— | 0.625 | <0.039 |
|  |  | 1.25 | 0.678 |
| 65 | $CH_3(CH_2)_{10}CONH$-(phenyl)-CO— (meta) | 5.0 | <0.039 |
| 66 | $CH_3(CH_2)_{10}CONH$-(phenyl)-CO—, OH | 1.25 | <0.039 |
| 67 | $CH_3(CH_2)_{10}CONH$-(phenyl, Cl, Cl)-CO— | 0.625 | <0.039 |
| 68 | $CH_3(CH_2)_{10}CONH$-(phenyl, I, I)-CO— | 1.25 | 0.078 |
| 69 | $CH_3(CH_2)_{10}CONH$-(phenyl, $CH_3$)-CO— | >20 | <0.039 |
| 70 | $CH_2(CH_2)_{10}CONH$-(phenyl, $CH_3$)-CO— | 20 | <0.039 |
| 71 | $CH_3(CH_2)_{10}CONH$-(phenyl, $CH_3O$)-CO— | — | — |
| 72 | $CH_3(CH_2)_{10}CONH$-(phenyl)-$CH_2$—CO— | 2.5 | 0.078 |

TABLE 5-continued

Antifungal Activity By the Agar Plate Disc Diffusion Test

| Compound | | MIC (μg/disc)* | |
|---|---|---|---|
| Example No. | $R^1$ or Formula III | Candida albicans A-26 | Trychophyton mentagrophytes #6 |
| 73 | $CH_3(CH_2)_{10}CONH$—⬡—$CH=CH-CO-$ | 1.25 | <0.039 |
| 74 | $CH_3(CH_2)_{10}CONH$—⬡—$CONHCH_2-CO-$ | 10 | 0.078 |
| 75 | $CH_3(CH_2)_{10}CONH$—(pyridine)—$CO-$ | 2.5 | 0.078 |
| 76 | $CH_3(CH_2)_5CONH(CH_2)_{10}-CO-$ | >20;80 | 0.625 |
| 77 | $CH_3CONH$—⬡—$CO-$ | >20;40 | 0.312 |
| 78 | $CH_3(CH_2)_5CONH$—⬡—$CO-$ | >20;160 | 1.25 |
| 79 | $CH_3(CH_2)_8CONH$—⬡—$CO-$ | 0.625 | — |
| 80 | $CH_3(CH_2)_{12}CONH$—⬡—$CO-$ | 1.25 | <0.039 |
| 81 | $CH_3(CH_2)_{14}CONH$—⬡—$CO-$ | 0.312 | <0.039 |

*Compounds were suspended in 0.01M sodium borate solution, pH 7.5. The compounds were tested at 20 μg/disc at top level and at two-fold dilutions until end points were reached. Incubation: 24 hours at 30° C.
**Measurable zones of inhibition with regrowth of organism around disc.

TABLE 6

In vitro activity of the N-(n-dodecanoyl)-p-amino-benzoyl (Example 64) and the N-(n-dodecanoyl)-5-amino-n-pentanoyl (Example 62) derivatives of A-30912A nucleus against 5 strains of *Candida albicans* by the agar dilution assay.

| | MIC (μg/ml) | | | | |
|---|---|---|---|---|---|
| Compound | A26 | SBH 16 | SBH 31 | SBH 28 | SBH 29 |
| Ex. 64 | 0.312 | 0.625 | 0.625 | 0.625 | 0.625 |
| Ex. 62 | 1.25 | 2.5 | 2.5 | 2.5 | 2.5 |

TABLE 7

Therapeutic Activity Against Candida Albicans A-26 in Mice*

| Compound | | $ED_{50}$ (mg/kg)** | Lowest Active Dose (mg/kg) |
|---|---|---|---|
| Example No. | $R^1$ of Formula III | | |
| 61 | $CH_3(CH_2)_{10}CONHCH(CH_2C_6H_5)-CO-$ | >40 | >40 |
| 62 | $CH_3(CH_2)_{10}CONH(CH_2)_4-CO-$ | 22 | 20 |
| 63 | $CH_3(CH_2)_{10}CONH(CH_2)_{10}-CO-$ | >40 | >40 |
| 64 | $CH_3(CH_2)_{10}CONH$—⬡—$CO-$ | 15 / 15 | 10 / ≦5 |
| 65 | $CH_3(CH_2)_{10}CONH$—⬡—$CO-$ (meta) | >40 | >40 |
| 66 | $CH_3(CH_2)_{10}CONH$—⬡(OH)—$CO-$ | >40 | 40 |
| 67 | $CH_3(CH_2)_{10}CONH$—⬡(Cl,Cl)—$CO-$ | 14 | 10 |
| 68 | $CH_3(CH_2)_{10}CONH$—⬡(I,I)—$CO-$ | >40 | 40 |

TABLE 7-continued

Therapeutic Activity Against Candida Albicans A-26 in Mice*

| Example No. | Compound R¹ of Formula III | $ED_{50}$ (mg/kg)** | Lowest Active Dose (mg/kg) |
|---|---|---|---|
| 69 | $CH_3(CH_2)_{10}CONH$—(ring with $CH_3$ and $CO$—) | >40 | >40 |
| 70 | $CH_2(CH_2)_{10}CONH$—(ring with $CH_3$)—$CO$— | >40 | >40 |
| 71 | $CH_3(CH_2)_{10}CONH$—(ring with $CH_3O$ and $CO$—) | >40 | >40 |
| 72 | $CH_3(CH_2)_{10}CONH$—(ring)—$CH_2$—$CO$— | >40 | 40 |
| 73 | $CH_3(CH_2)_{10}CONH$—(ring)—$CH=CH$—$CO$— | 24 | 20 |
| 74 | $CH_3(CH_2)_{10}CONH$—(ring)—$CONHCH_2$—$CO$— | >40 | >40 |
| 75 | $CH_3(CH_2)_{10}CONH$—(N-ring)—$CO$— | >40 | >40 |
| 76 | $CH_3(CH_2)_5CONH(CH_2)_{10}$—$CO$— | >40 | >40 |
| 77 | $CH_3CONH$—(ring)—$CO$— | >40 | >40 |
| 78 | $CH_3(CH_2)_5CONH$—(ring)—$CO$— | >40 | >40 |
| 79 | $CH_3(CH_2)_8CONH$—(ring)—$CO$— | 26 | 5 |
| 80 | $CH_3(CH_2)_{12}CONH$—(ring)—$CO$— | 11 | 2.5 |
| 81 | $CH_3(CH_2)_{14}CONH$—(ring)—$CO$— | 7 | 5 |
| 86 | $CH_3(CH_2)_6CONH$—(ring with $Cl$)—$CO$— | 29 | 10 |
| 88 | $CH_3(CH_2)_6CONH$—(ring with $Cl$, $Cl$)—$CO$— | >40 | 20 |

*Dosage Schedule: 40, 20, 15, and 10 mg/kg. Dosages given 0, 4, and 24 hours post injection as suspension of test compound in 30% PEG-H₂O. Number of mice receiving test compounds at each dosage level: 6 mice per group. Number of mice in control (untreated) group: 10 mice per group.
**As measured by increase in survival time of treated animals versus control, calculated by method of Reed V. Mueuch, American J. Hygiene, 493 (1938).

TABLE 8

Blood Levels after Administration in Mice

| Example No. | Compound R¹ in Formula III | Blood Levels* (μg/ml) |
|---|---|---|
| 61 | $CH_3(CH_2)_{10}CONHCH(CH_2C_6H_5)$—$CO$— | 0 |
| 62 | $CH_3(CH_2)_{10}CONH(CH_2)_4$—$CO$— | 0 |
| 63 | $CH_3(CH_2)_{10}CONH(CH_2)_{10}$— | 0.40(0) |
| 64 | $CH_3(CH_2)_{10}CONH$—(ring)—$CO$— | 0.83 |

TABLE 8-continued
Blood Levels after Administration in Mice

| Example No. | Compound $R^1$ in Formula III | Blood Levels* ($\mu$g/ml) |
|---|---|---|
| 65 | $CH_3(CH_2)_{10}CONH$—[pyridine]—CO— | 0 |
| 66 | $CH_3(CH_2)_{10}CONH$—[phenyl, OH]—CO— | 0 |
| 67 | $CH_3(CH_2)_{10}CONH$—[phenyl, Cl, Cl]—CO— | 0.53 |
| 68 | $CH_3(CH_2)_{10}CONH$—[phenyl, I, I]—CO— | 0.34 |
| 69 | $CH_3(CH_2)_{10}CONH$—[phenyl, $CH_3$]—CO— | 0 |
| 70 | $CH_2(CH_2)_{10}CONH$—[phenyl, $CH_3$]—CO— | 0 |
| 71 | $CH_3(CH_2)_{10}CONH$—[phenyl, $CH_3O$]—CO— | — |
| 72 | $CH_3(CH_2)_{10}CONH$—[phenyl]—$CH_2$—CO— | 0.34 |
| 73 | $CH_3(CH_2)_{10}CONH$—[phenyl]—CH=CH—CO— | 1.31 |
| 74 | $CH_3(CH_2)_{10}CONH$—[phenyl]—$CONHCH_2$—CO— | 0.64 |
| 75 | $CH_3(CH_2)_{10}CONH$—[pyridine, —CO—]  | 0 |
| 76 | $CH_3(CH_2)_5CONH(CH_2)_{10}$—CO— | 0 |
| 77 | $CH_3CONH$—[phenyl]—CO— | 0 |
| 78 | $CH_3(CH_2)_5CONH$—[phenyl]—CO— | — |
| 79 | $CH_3(CH_2)_8CONH$—[phenyl]—CO— | — |
| 80 | $CH_3(CH_2)_{12}CONH$—[phenyl]—CO— | 6.5 |
| 81 | $CH_3(CH_2)_{14}CONH$—[phenyl]—CO— | 36 |

*Four hours after administration of test compound at dose of 416 mg/kg by gavage as suspension of compound in 33% PEG 400-$H_2O$). Compound determined by bioassay vs. *Aspergillus montevidensis* A-35137.

EXAMPLE 93

Preparation of A-30912A Nucleus

A. Fermentation of *Actinoplanes utahensis* NRRL 12052

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Baby oatmeal | 60.0 g |
| Yeast | 2.5 g |
| $K_2HPO_4$ | 1.0 g |

-continued

| MEDIUM A | |
|---|---|
| Ingredient | Amount |
| Czapek's mineral stock* | 5.0 ml |
| Agar | 25.0 g |
| Deionized water | q.s. to 1 liter | pH before autoclaving is about 5.9; adjust to pH 7.2 by addition of NaOH; after autoclaving, pH is about 6.7.
*Czapek's mineral stock has the following composition:

| Ingredient | Amount |
|---|---|
| FeSO$_4$ . 7H$_2$O (dissolved in 2 ml conc HCl) | 2 g |
| KCl | 100 g |
| MgSO$_4$ . 7H$_2$O | 100 g |
| Deionized water | q.s. to 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Dextrose | 12.5 g |
| Corn starch | 5.0 g |
| Meat peptone | 5.0 g |
| Blackstrap molasses | 2.5 g |
| MgSO$_4$ . 7H$_2$O | 0.25 g |
| CaCO$_3$ | 1.0 g |
| Czapek's mineral stock | 2.0 ml |
| Agar | 20.0 g |
| Deionized water | q.s. to 1 liter |

*N—Z—Amine A, Humko Sheffield Chemical, Lyndhurst, N.J.

The slant is inoculated with *Actinoplanes utahensis* NRRL 12052 and the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| K$_2$HPO$_4$ | 1.0 g |
| Czapek's mineral stock | 5.0 ml |
| Deionized water | q.s. to 1 liter |
| adjust to pH 7.4 with NaOH; after autoclaving, pH is about 6.8 | |

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen, Cryobiol 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH$_2$PO$_4$ | 0.5 |
| K$_2$HPO$_4$ | 1.2 |
| MgSO$_4$ . 7H$_2$O | 0.25 |
| Tap water | q.s. to 1 liter |

The pH of the medium is about 6.9 after sterilization by autoclaving at 121° C. for 45 minutes at about 16–18 psi.

| MEDIUM II | |
|---|---|
| Ingredient | Amount (g/L) |
| Sucrose | 30.0 |
| Peptone | 5.0 |
| K$_2$HPO$_4$ | 1.0 |
| KCl | 0.5 |
| MgSO$_4$ . 7H$_2$O | 0.5 |
| FeSO$_4$ . 7H$_2$O | 0.002 |
| Deionized water | q.s. to 1 liter |
| Adjust to pH 7.0 with HCl; after autoclaving, pH is about 7.0 | |

| MEDIUM II | |
|---|---|
| Ingredient | Amount (g/L) |
| Glucose | 20.0 |
| NH$_4$Cl | 3.0 |
| Na$_2$SO$_4$ | 2.0 |
| ZnCl$_2$ | 0.019 |
| MgCl$_2$ . 6H$_2$O | 0.304 |
| FeCl$_3$ . 6H$_2$O | 0.062 |
| MnCl$_2$ . 4H$_2$O | 0.035 |
| CuCl$_2$ . 2H$_2$O | 0.005 |
| CaCO$_3$ | 6.0 |
| KH$_2$PO$_4$* | 0.67 |
| Tap water | q.s. to 1 liter |

*Sterilized separately and added aseptically

Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level above 30% of air saturation at atmospheric pressure.

B. Deacylation of Antibiotic A-30912 Factor A

A fermentation of *A. utahensis* is carried out as described in Sect. A, using slant medium A and production medium I and incubating the production medium for about 42 hours. A-30912 factor A (340 g. of crude substrate which contained about 19.7 g. of A-30912 factor A, dissolved in 1.5 L ethanol) is added to the fermentation medium.

Deacylation of A-30912 factor A is monitored by assay against *Candida albicans*. The fermentation is allowed to continue until deacylation is complete as indicated by disappearance of activity vs. *C. albicans*.

c. Isolation of A-30912A Nucleus

Whole fermentation broth (100 liters), obtained as described in Sect. B and containing nucleus from about 20 g of A-30912 factor A, is filtered. The mycelial cake is discarded. The clear filtrate thus obtained (about 93 liters) is passed through a column containing 4.5 liters of HP-20 resin (DIAION High Porous Polymer, HP-Series, Mitsubishi Chemical Industries Limited, Tokyo, Japan) at a rate of 200 ml/minute. The effluent thus obtained is discarded. The column is then washed with up to eight column volumes of deionized water at pH 6.5-7.5 to remove residual filtered broth. This wash water is discarded. The column is then eluted with a water:methanol (7:3) solution (85 liters) at a rate of 200-300 ml/minute.

Elution is monitored using the following procedure: Two aliquots are taken from each eluted fraction. One of the aliquots is concentrated to a small volume and is treated with an acid chloride such as myristoyl chloride. This product and the other (untreated) aliquot are assayed for activity against *Candida albicans*. If the untreated aliquot does not have activity and the acylated aliquot does have activity, the fraction contains A-30912A nucleus. The eluate containing the A-30912A nucleus is concentrated under vacuum to a small volume and lyophilized to give approximately 97 grams of crude nucleus.

D. Purification of A-30912A Nucleus by Reversed-Phase Liquid Chromatography

Crude A-30912A nucleus (25 grams), obtained as described in Section C, is dissolved in 300 ml of water-:acetonitrile:acetic acid:pyridine (96:2:1:1). This solution is chromatographed on a 4-liter stainless-steel column (8 cm×80 cm) filled with Lichroprep RP-18, particle size 25-40 microns (MC/B Manufacturing Chemists, Inc. E/M, Cincinnati, OH). The column is part of a Chromatospac Prep 100 unit (Jobin Yvon, 16-18 Rue du Canal 91160 Longjumeau, France). The column is operated at a pressure of 90-100 psi, giving a flow rate of about 60 ml/minute, using the same solvent. Separation is monitored at 280 nm using a UV monitor (ISCO Absorption Monitor Model UA-5, Instrument Specialist Co., 4700 Superior Ave., Lincoln, Nebr. 68504) with an optical unit (ISCO Type 6). Fractions having a volume of about 500 ml are collected each minute.

On the basis of absorption at 280 nm, fractions containing A-30912A nucleus are combined, evaporated under vacuum and lyophilized to give 2.6 grams of nucleus. The amount of solvent required to complete this chromatographic separation process varies from 7-8 liters.

E. Characteristics of A30912A nucleus (a) Empirical formula: $C_{34}H_{51}N_7O_{15}$.
(b) Molecular weight: 797.83
(c) Soluble in water, dimethylformamide, dimethylsulfoxide, and methanol; insoluble in chloroform, toluene, and diethylether.
(d) Infrared absorption spectrum (KBr disc.)
Shows absorption maxima at:
3340 broad (OH, H-bonded); 2970, 2930, and 2890 (CH stretch, aliphatic $CH_3$, $CH_2$, CH groups) 1660 and 1625 (several carbonyls C=O); 1510-1550; 1430-1450 (CH wag); 1310-1340; 1230-1260; 1080; 835, 650 broad, and 550 broad $cm^{-1}$.
(e) Electrometric titration in 66% aqueous dimethylformamide indicates the presence of a titratable group with a $pK_a$ value of about 7.35 (initial pH 7.32).
(f) HPLC retention time (K'):11.52 min. under following conditions.
Column: 4×300 mm
Packing: silica gel/$C_{18}$
Solvent: ammonium acetate:acetonitrile: water (1:2:97)
Flow Rate: 3 ml/min
Pressure: 2500 psi
Detector: variable wavelength UV at 230 nm
Sensitivity: 0-0.4 A.U.F.S.

EXAMPLE 94

A-30912A nucleus is prepared and purified by the method of Example 93 except that tetrahydro-A-30912A is used as the substrate.

EXAMPLE 95

A-30912A nucleus is prepared and purified by the method of Example 93 except that aculeacin A is used as the substrate.

EXAMPLE 96

Preparation of the A-42355 Antibiotic Complex

A. Shake-Flask Fermentation

A culture of *Aspergillus nidulans* var. roseus NRRL 11440 is prepared and maintained on an agar slant prepared with medium having the following composition:

| Ingredient | Amount |
| --- | --- |
| Glucose | 5 g |
| Yeast extract | 2 g |
| $CaCO_3$ | 3 g |
| Vegetable juice* | 200 ml |
| Agar** | 20 g |
| Deionized water (initial pH 6.1) | q.s. to 1 liter |

*V-8 Juice, Campbell Soup Co., Camden, N.J.
**Meer Corp.

The slant is inoculated with *Aspergillus nidulans* var. roseus NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculate 55 ml of vegetative medium in a 250-ml flask. The vegetative medium has the following composition:

| Ingredient | Amount |
| --- | --- |
| Sucrose | 25 g |
| Blackstrap molasses | 36 g |
| Corn-steep liquor | 6 g |
| Malt extract | 10 g |
| $K_2HPO_4$ | 2 g |
| Enzymatic hydrolysate of casein* | 10 g |
| Tap water (initial pH 6.5-6.7) | 1100 ml |

*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows:

The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

| MEDIUM IV | |
| --- | --- |
| Ingredient | Amount |
| $ZnSO_4 \cdot 7H_2O$ | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| $Na_2HPO_4$ | 4.5 g/L |
| $MgSO_4 \cdot 7H_2O$ | 5.5 g/L |
| $FeSO_4 \cdot 7H_2O$ | 0.1 g/L |
| Cottonseed oil | 40.0 ml |
| (Antifoam)**** | 1.0 ml |
| Tap water (initial pH 6.8-7.0) | 1000.0 ml |

*O.M. Peptone, Amber Laboratories, Juneau, Wisc.
**Stadex 11, A.E. Staley Co., Decatur, Ill.
***N-Z-Amine A, Humko Sheffield Chemical, Lyndhurst, N.J.
**** P2000, Dow Corning, Midland, Michigan

| MEDIUM V | |
| --- | --- |
| Ingredient | Amount |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 \cdot 7H_2O$ | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
| --- | --- |
| Sucrose | 25 g |
| Blackstrap molasses | 25 g |
| Corn-steep liquor | 6 g |
| Enzymatic hydrolysate of casein* | 10 g |
| Malt extract | 10 g |
| $K_2HPO_4$ | 2 g |
| Tap water (initial pH 6.1) | 1000 ml |

*N-Z-Case

EXAMPLE 97

Separation of the A-42355 Antibiotic Complex

Whole fermentation broth (4127 liters), obtained by the method described in Example 96 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 98

Isolation of A-30912 Factor A

The co-pending application of Karl H. Michel entitled RECOVERY PROCESS FOR A-30912 ANTIBIOTICS, Ser. No. 103,014, filed Dec. 13, 1979, describes the reversed-phase high performance, low pressure liquid chromatography (HPLPLC) using silica gel/$C_{18}$ adsorbent as a preferred method for the final purification of A-30912 factor A.

A-42355 antibiotic complex (1 g), prepared as described in Example 97, is dissolved in 7 ml of methanol:water:acetonitrile (7:2:1). This solution is filtered and introduced onto a 3.7-cm I.D.×35-cm glass column [Michel-Miller High Performance Low Pressure (HPLPLC) Chromatography Column, Ace Glass Incorporated, Vineland, NJ 08360] packed with LP-1/$C_{18}$ silica gel reversed-phase resin (10–20 microns), prepared as described in Example 99, through a loop with the aid of a valve system. The column is packed in methanol:water:acetonitrile (7:2:1) by the slurry-packing procedure described in Example 100. An F.M.I. pump with valveless piston design (maximum flow 19.5 ml/minute) is used to move the solvent through the column at a flow rate of 9 ml/minute at ca. 100 psi, collecting fractions every minute. Elution of the antibiotic is monitored at 280 nm by using a UV monitor (ISCO Model UA-5, Instrument Specialist Co., 4700 Superior Ave., Lincoln, Nebr. 68504) with an optical unit (ISCO Type 6).

The individual A-30912 factors can be identified by the use of thin-layer chromatography (TLC). The $R_f$ values of A-30912 factors A-G, using silica gel (Merck, Darmstadt) TLC, a benzene:methanol (7:3) solvent system, and *Candida albicans* bioautography are given in Table 9.

TABLE 9

| A-30912 Factor | $R_f$ Value |
| --- | --- |
| A | 0.35 |
| B | 0.45 |
| C | 0.54 |
| D | 0.59 |
| E | 0.27 |
| F | 0.18 |

TABLE 9-continued

| A-30912 Factor | $R_f$ Value |
| --- | --- |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table 10.

TABLE 10

| A-30912 Factor | $R_f$ Values - Solvent Systems | | | |
| --- | --- | --- | --- | --- |
| | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a: ethyl acetate:methanol (3:2)
b: ethyl acetate:methanol (7:3)
c: acetonitrile:water (95:5)
d: ethyl acetate:ethanol:acetic acid (40:60:0.25)

A-30912 factors A, B, D and H can also be indentified by analytical HPLPLC using the following conditions:

| | |
| --- | --- |
| Column: | glass, 0.8 × 15.0 cm |
| Packing: | Nucleosil® 10-$C_{18}$ (Machery-Nagel and Company); packed using slurry-packing procedure of Example 73 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table 11.

TABLE 11

| A-30912 Factor | Retention Time (seconds) |
| --- | --- |
| A | 792 |
| B | 870 |
| H | 990 |
| D | 1,140 |

EXAMPLE 99

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask. This is to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 100

Slurry Packing Procedure for Michel-Miller Columns

General Information

This procedure is employed for packing reversed phase silica gel $C_{18}$ resins, such as that described in Example 99.

Generally, a pressure of less than 200 psi and flow rates between 5–40 ml/minute are required for this slurry packing technique; this is dependent on column volume and size. Packing pressure should exceed the pressure used during actual separation by 30–50 psi; this will assure no further compression of the adsorbent during separation runs.

A sudden decrease in pressure may cause cracks or channels to form in the packing material, which would greatly reduce column efficiency. Therefore, it is important to let the pressure drop slowly to zero whenever the pump is turned off.

The approximate volume of columns (Ace Glass Cat. No., unpacked) are No. 5795-04, 12 ml; No. 5795-10, 110 ml; No. 5795-16, 300 ml; No. 5795-24, 635 ml; and No. 5796-34, 34 ml.

The time required to pack a glass column will vary from minutes to several hours depending on column size and the experience of the scientist.

EXAMPLE

1. Connect glass column to a reservoir column via coupling (volume of reservoir column should be twice that of the column). Place both columns in vertical positions (reservoir column above).

2. Weigh out packing material (ca. 100 g for 200 ml column).

3. Add ca. five volumes of solvent to packing material; use a mixture of 70–80% methanol and 20–30% water.

4. Shake well until all particles are wetted, let stand overnight or longer to assure complete soaking of particles by solvent. Decant supernatant liquid.

5. Slurry the resin with sufficient solvent to fill reservoir column. Pour swiftly into reservoir. The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.

6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).

7. Continue until column is completely filled with adsorbent. Pressure should not exceed maximum tolerance of column during this operation (ca. 200 psi for large columns and 300 psi for analytical columns). In most cases, pressures less than 200 psi will be sufficient.

8. Should pressure exceed maximum values, reduce flow-rate; pressure will drop.

9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure. Always allow pressure to decrease slowly after turning off pump—this will prevent formation of any cracks or channels in the packing material.

10. Relieve pressure and disconnect precolumn carefully. With small spatula remove a few mm (2–4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 101

Preparation of Tetrahydro-A-30912A

A-30912 factor A is dissolved in ethanol. $PtO_3$ in absolute ethanol is reduced to form Pt, which in turn is used to reduce the A-30912 factor A catalytically, using hydrogenation under positive pressure until the reaction is complete (about 2–3 hours). The reaction mixture is filtered and concentrated under vacuum. The residue is dissolved in a small amount of tert-butanol and lyophilized to give tetrahydro-A-30912A.

What is claimed is:

1. A compound of the formula:

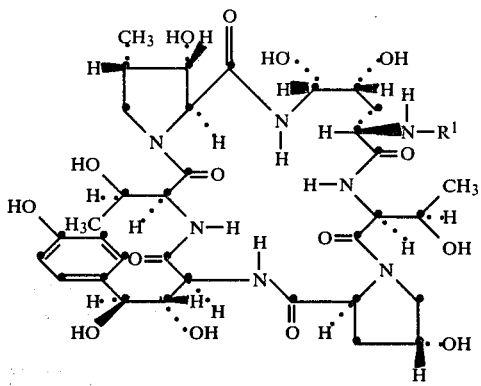

wherein

R¹ is an N-alkanoyl amino acyl group of the formula

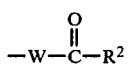

wherein:

W is a divalent aminoacyl radical of the formula:

(a) 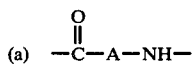

wherein A is $C_1$-$C_{10}$ alkylene or $C_5$-$C_6$ cycloalkylene;

(b) 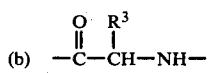

wherein R³ is hydroxymethyl, hydroxyethyl, mercaptomethyl, mercaptoethyl, methylthioethyl, 2-thienyl, 3-indole-methyl, phenyl, benzyl, or substituted phenyl or substituted benzyl in which the benzene ring thereof is substituted with chloro, bromo, iodo, nitro, $C_1$-$C_3$ alkyl, hydroxy, $C_1$-$C_3$ alkylthio, carbamyl, or $C_1$-$C_3$ alkylcarbamyl;

(c) 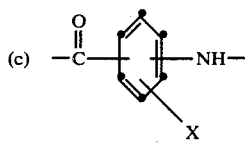

wherein X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamoyl, or $C_1$-$C_3$ alkylcarbamyl;

(d) 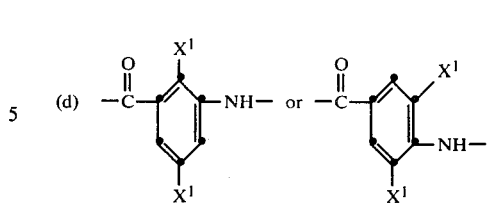

wherein $X^1$ is chloro, bromo, or iodo;

(e) 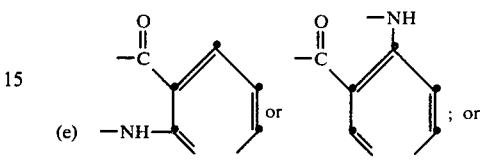

(f) 

wherein B is a divalent radical of the formula; —(CH₂)ₙ—, wherein n is an integer from 1 to 3; —CH=CH—; —CH=CH—CH₂—; or $$-\overset{O}{\underset{\|}{C}}NHCH_2-$$

and R² is $C_1$-$C_{17}$ alkyl or $C_2$-$C_{17}$ alkenyl.

2. A compound as defined in claim 1 wherein R¹ is

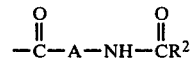

wherein A is $C_1$-$C_{10}$ alkylene and R² is straight chain $C_1$-$C_{17}$ alkyl.

3. The compound as defined in claim 2 wherein R¹ is N-(n-dodecanoyl)-5-amino-n-pentanoyl.

4. The compound as defined in claim 2 wherein R¹ is N-(n-dodecanoyl)-11-amino-n-hendecanoyl.

5. The compound as defined in claim 2 wherein R¹ is N-(n-heptanoyl)-11-amino-n-hendecanoyl.

6. A compound as defined in claim 1 wherein R¹ is

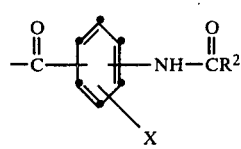

wherein X is hydrogen and R₂ is straight chain $C_1$-$C_{17}$ alkyl.

7. The compound as defined in claim 6 wherein R¹ is N-(n-dodecanoyl)-p-aminobenzoyl.

8. The compound as defined in claim 6 wherein R¹ is N-(n-dodecanoyl)-m-aminobenzoyl.

9. The compound as defined in claim 6 wherein R¹ is N-(acetyl)-p-aminobenzoyl.

10. The compound as defined in claim 6 wherein R¹ is N-(n-heptanoyl)-p-aminobenzoyl.

11. The compound as defined in claim 6 wherein $R^1$ is N-(n-decanoyl)-p-aminobenzoyl.

12. The compound as defined in claim 6 wherein $R^1$ is N-(n-tetradecanoyl)-p-aminobenzoyl.

13. The compound as defined in claim 6 wherein $R^1$ is N-(n-hexadecanoyl)-p-aminobenzoyl.

14. A compound as defined in claim 1 wherein $R^1$ is

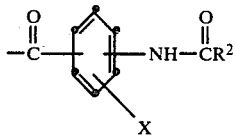

wherein X is chloro, bromo, iodo, nitro, $C_1$–$C_3$ alkyl, hydroxy, $C_1$–$C_3$ alkoxy, mercapto, $C_1$–$C_3$ alkylthio, carbamyl, or $C_1$–$C_3$ alkylcarbamyl, and $R^2$ is straight chain $C_1$–$C_{17}$ alkyl.

15. The compound as defined in claim 14 wherein $R^1$ is N-(n-dodecanoyl)-4-amino-2-hydroxybenzoyl.

16. The compound as defined in claim 14 wherein $R^1$ is N-(n-dodecanoyl)-3-amino-4-methylbenzoyl.

17. The compound as defined in claim 14 wherein $R^1$ is N-(n-dodecanoyl)-4-amino-3-methylbenzoyl.

18. The compound as defined in claim 14 wherein $R^1$ is N-(n-dodecanoyl)-3-amino-4-methoxybenzoyl.

19. The compound as defined in claim 1 wherein $R^1$ is N-(n-dodecanoyl)-3-amino-2,5-dichlorobenzoyl.

20. The compound as defined in claim 1 wherein $R^1$ is N-(n-dodecanoyl)-4-amino-3,5-diodobenzoyl.

21. The compound as defined in claim 1 wherein $R^1$ is N-(n-dodecanoyl)-p-aminophenylacetyl.

22. The compound as defined in claim 1 wherein $R^1$ is N-(n-dodecanoyl)-p-aminocinnamoyl.

23. The compound as defined in claim 1 wherein $R^1$ is N-(n-dodecanoyl)-p-aminohippuryl.

24. The compound as defined in claim 1 wherein $R^1$ is N-(n-dodecanoyl)-2-aminonicotinyl.

25. The compound as defined in claim 1 wherein $R^1$ is N-(n-dodecanoyl)phenylalanyl.

* * * * *